(12) United States Patent
Ehwald et al.

(10) Patent No.: US 7,461,671 B2
(45) Date of Patent: Dec. 9, 2008

(54) AUTOMATIC SAMPLE COLLECTOR

(75) Inventors: Rudolf Ehwald, Berlin (DE); Dietmar Lerche, Berlin (DE); Holger Woehlecke, Berlin (DE)

(73) Assignees: Humboldt-Universitaet Zu Berlin, Berlin (DE); L.U.M. GmbH, Berlin (DE)

( * ) Notice: Subject to any disclaimer, the term of this patent is extended or adjusted under 35 U.S.C. 154(b) by 362 days.

(21) Appl. No.: 10/510,485

(22) PCT Filed: Mar. 21, 2003

(86) PCT No.: PCT/EP03/03014

§ 371 (c)(1),
(2), (4) Date: Oct. 7, 2004

(87) PCT Pub. No.: WO03/085395

PCT Pub. Date: Oct. 16, 2003

(65) Prior Publication Data

US 2005/0161112 A1 Jul. 28, 2005

(30) Foreign Application Priority Data

Apr. 9, 2002 (DE) .................... 102 21 957

(51) Int. Cl.
*B65B 1/04* (2006.01)
*A61M 1/00* (2006.01)
(52) U.S. Cl. ............. 141/244; 141/5; 141/35; 141/198; 141/237; 604/323

(58) Field of Classification Search ............. 141/4–8, 141/35, 67, 192, 198, 234–238, 242–244; 604/322–324; 137/177, 197
See application file for complete search history.

(56) References Cited

U.S. PATENT DOCUMENTS

| 2,884,021 | A | | 4/1959 | Ginsburg |
| 3,111,968 | A | * | 11/1963 | Headrick .................... 141/21 |
| 3,307,371 | A | | 3/1967 | Andros |
| 3,982,538 | A | * | 9/1976 | Sharpe ...................... 604/320 |
| 4,012,209 | A | * | 3/1977 | McDowell et al. ........... 96/325 |

(Continued)

FOREIGN PATENT DOCUMENTS

EP 0 282 840 A 9/1988

(Continued)

*Primary Examiner*—Timothy L Maust
(74) *Attorney, Agent, or Firm*—Rothwell, Figg, Ernst & Manbeck, P.C.

(57) ABSTRACT

This invention relates to an automatic sample collector for liquids which are discharged from a chromatographic column, a dialysis apparatus, or a reaction container, for example, and are consecutively collected at a give volume division, a method for collecting samples of a liquid in a predefined chronological sequence, and uses of the inventive sample collector. The volume is divided by assigning one or several gas-permeable liquid barriers (4, 5) to each collection container (3). The sample collector can be produced as one piece which is for single use and is made of polypropylene, Teflon, or other suitable materials. The inventive sample collector has the advantage that it requires no source of energy and can be autoclaved and miniaturized, among other things. The design of the inventive sample collector makes it possible to keep the content of the collection containers free from oxygen or immediately freeze the liquid flowing into the collection containers.

21 Claims, 2 Drawing Sheets

U.S. PATENT DOCUMENTS

| | | |
|---|---|---|
| 4,258,758 A | 3/1981 | Nygards |
| 4,490,982 A | 1/1985 | Christmas |
| 4,754,786 A * | 7/1988 | Roberts ......................... 141/1 |
| 5,093,269 A * | 3/1992 | Leichnitz et al. ............ 436/178 |
| 5,701,937 A | 12/1997 | Bourboulou et al. |
| 2003/0099576 A1 * | 5/2003 | Li et al. ...................... 422/100 |

FOREIGN PATENT DOCUMENTS

| | | |
|---|---|---|
| FR | 2 284 872 A | 4/1976 |
| WO | WO 00 22436 A | 4/2000 |
| WO | WO 01 78893 A | 10/2001 |

* cited by examiner

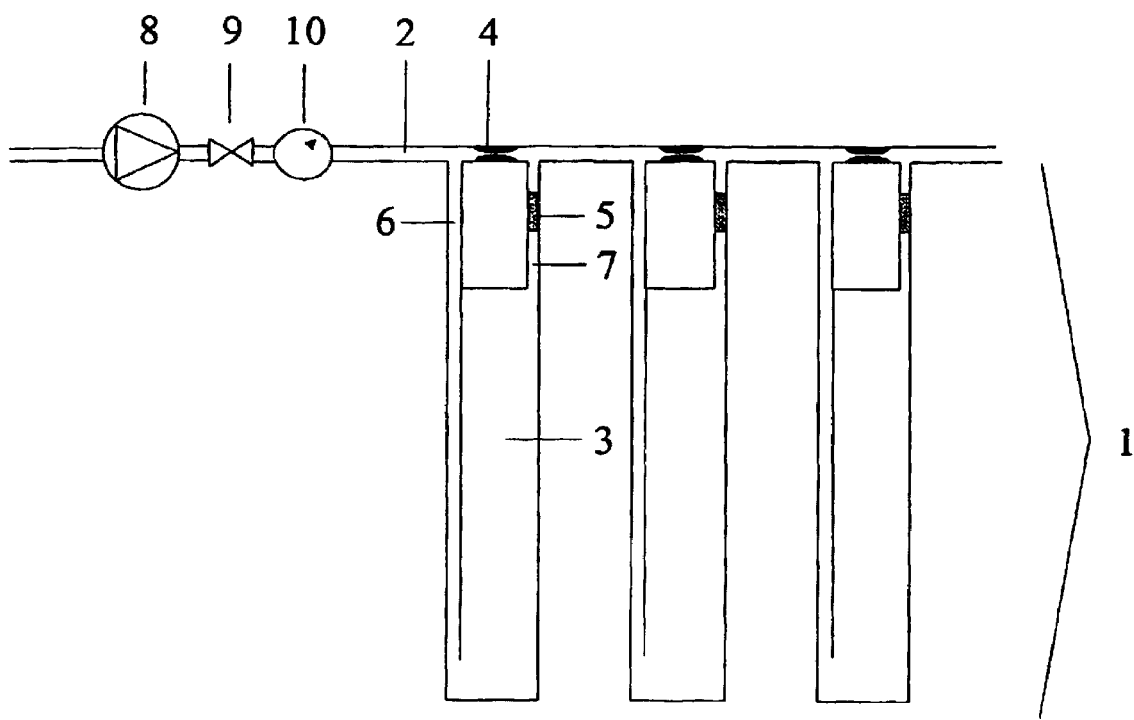
Figur 1a
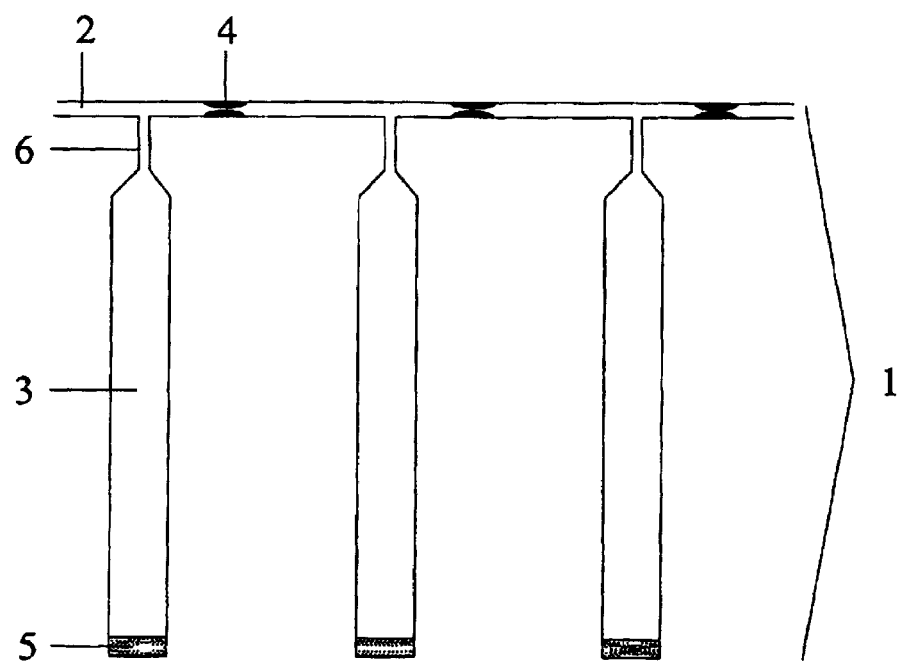
Figur 1b

AUTOMATIC SAMPLE COLLECTOR

CROSS REFERENCE TO RELATED APPLICATION

This application is a 35 USC § 371 National Phase Entry Application from PCT/EP03/03014, filed Mar. 21, 2003, and designating the U.S.

The invention relates to an automatic sample collector, a method to collect samples, as well as uses of the sample collector in accordance with the invention.

To collect liquid volume fractions of the eluate of chromatography columns or the effluent of a reaction container, such as a bio reactor, for example, fraction collections are generally used, and the volume dosing is performed with a siphon, a drop counter or the flow time at constant flow rate, for example. These apparatuses, which are developed for laboratory use, comprise electric motors and various other mechanical constructions with movable elements to position the collection containers and the effluent relative to one another when the containers are changed. Commercial fraction collectors do not prevent contact between atmospheric air and the microorganisms in said air and the liquid to be collected and portioned. They cannot be used without additional and high-effort protective measures if the substances to be analyzed are volatile or oxidation-sensitive or easily decomposed by microorganisms or enzymes. Commercial fraction collectors have to be modified for battery operation if they are to be used in the field. They cannot be used under water.

The object to be attained by the invention was to provide an apparatus and a method to collect liquid samples and store them in a closed container, with the apparatus being simple and economical to produce, and suitable for miniaturization and coupling with other elements such as cooling means, and the method being suitable to enable an effective automation of the collection as well as of very small samples and being realizable without the addition of electric energy.

Another object to be attained by the invention is to develop new application areas for automatic sample collectors.

In accordance with the invention, the object of the invention is attained with an automatic sample collector having the characteristics of Claim 1 and a method to collect liquid samples having the characteristics listed in claim 15.

The goal of the invention is to provide an automatic apparatus that is potentially independent of the energy supply and a method for collecting liquid samples which is potentially independent of the energy supply, which make it possible to deposit defined volume fractions from a flow of liquid without requiring a mechanical construction with movable elements to do so, and which seal off the liquid to be fractioned and collected from external medium and protect it from contact with the oxygen-containing air or microorganisms and/or active enzymes. The automatic sample collector allows for the chronological deposition of samples with varying volumes, even very small samples comprising only a few µl, and can potentially be miniaturized itself. Furthermore, the automatic sample collector allows for freezing the collected samples, if necessary, in connection with a cooling apparatus.

The automatic sample collector is characterized in that one or a plurality of collection containers arranged in series at a supply line are connected by a permeable liquid inlet and said supply line has a gas-permeable liquid barrier after each liquid inlet. Furthermore, an apparatus in the collection container to discontinue the flow of liquid after the collection container has been filled is indispensable.

The gas-permeable liquid barrier in the supply line allows the gas that was displaced by the sample liquid to flow out of the supply line in dry condition and then collapses after contact with the liquid and after exceeding a critical pressure difference, i.e., if becomes permeable for the sample liquid. It is known that in the case of an aqueous sample solution, thin capillaries or coarse particle filters made of a hydrophobic material such as polyethylene, Teflon or the like with a pore- or capillary radius in the range of 10 to 100 micrometers have these properties. There are various other known options for creating a gas-permeable liquid barrier with a defined and limited pressure resistance, such as coating a steel cannula or glass capillary with hydrophobic material or inserting a package of hydrophobic particles into the supply line. It is known that for many non-aqueous liquids, gas-permeable liquid barriers on the basis of wetting resistors at the interior wall of pores or capillaries, which collapse at a defined pressure difference, can also be set up in a defined manner. A condition for this is that the critical angle of the liquid in the capillaries or pores assumes a value of over 90°. Gas-permeable liquid barriers can also be created on the basis of the swelling of a gel or solid matter. Even if these liquid barriers do not collapse at a critical pressure, a gas-permeable liquid barrier can be created with the help of a bypass with pressure relief valve, which collapses at a critical pressure. Therefore, the invention is not limited to liquids for a gas-permeable capillary- or pore system with sufficient and limited capillary depression.

The functioning of the sample collector in accordance with the invention requires that the flow in the liquid inlet to the collection container is interrupted after said collection container is filled. Furthermore, it is normally also required that the gas displaced in the filling of the collection container can escape from the collection container or that there is a gas discharge from the collection container. The gas discharge may be obsolete if the liquid freezes in the collection container and the liquid discharge ices at a specific filing level, which will be discussed in greater detail below. In accordance with the invention, the gas discharge at the collection container may contain a second gas-permeable liquid barrier or be designed as such, with said second gas-permeable liquid barrier collapsing at a clearly higher pressure difference than the gas-permeable liquid barrier in the supply line. The liquid barrier in the gas discharge ends the flow of the liquid through the liquid inlet after the collection container has been filled. The sample collector in accordance with the invention requires no movable stationary parts for the chronological deposit of liquid samples from an existing flow.

The invention is explained in the following by means of the figures in the examples of embodiments.

FIG. 1a and FIG. 1b show two different options to realize the gas discharge from the collection containers in the sample collector in accordance with the invention.

FIGS. 1a and 1b are directed to a different embodiment of the device for interrupting the liquid flow being realized as a liquid barrier 5.

Figure 1C:
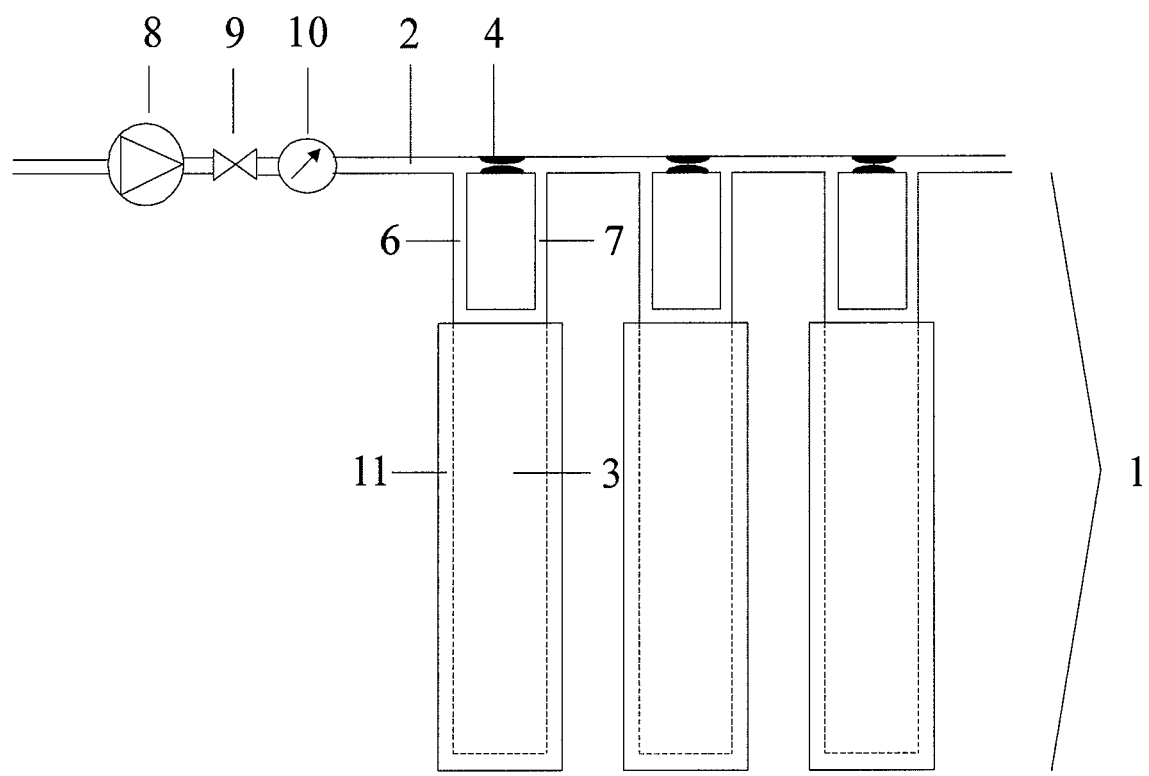
FIG. 1c shows one embodiment of a device for interrupting the liquid flow into the collection containers 3 realized as a cooling apparatus 11.

FIG. 1a schematically shows an automatic sample collector where the gas discharge occurs through the non-filled part in the supply line. FIG. 1b schematically shows an automatic sample collector where the gas discharge occurs in a way other than through the supply line.

In the embodiment shown in FIG. 1a, each collection container 3 has a liquid inlet 6 that starts at the supply line 2, as well as a subsequent gas discharge 7 that leads to the supply line 2 in the direction of the flow. Between the branch-off of the liquid inlet 6 and the merging of the gas discharge 7, the supply line 2 has the gas-permeable liquid barrier 4, which collapses at a defined and limited pressure difference.

To prevent the outflow of the liquid through the gas discharge 7 after a collection container 3 has been filled, the gas discharge 7 has a gas-permeable liquid barrier 5, and the collapse of said liquid barrier requires a greater pressure difference than the collapse of the liquid barrier 4. The dynamic pressure of the liquid after the filling of the collection container 3 therefore causes the liquid barrier 4 to collapse, which initiates the filling of the next collection container 3. The supply line 2 can be connected to a delivery apparatus 8. If a pressure- or negative pressure container is used as a delivery apparatus instead of a pump, the introduction of a valve 9 is required for certain applications. The pump 8 or the valve 9 can be controlled by a timer, such as a time switch or a timing program, for specific applications. For specific applications, it makes sense to provide a pressure sensor 10 in the supply line 2 upstream of the first collection container 3. The latter can detect the increase of pressure in the supply line after the filling of each collection container and the decrease of the pressure in the supply line 2 at the collapse of each gas-permeable liquid barrier 4 in the supply line 2. With the help of a suitable control, said change in pressure can be used as a signal to interrupt the flow of liquid by switching off the pump 8 or sealing the valve 9.

FIG. 1b shows schematically an especially simple development of the sample collector 1, where the gas that escapes during the filling of the samples is emitted directly into the atmosphere. Likewise, if required by the application, it is also possible to provide a special gas discharge channel or a closed gas space to hold the discharged gas. In said development, the collection container 3 and the supply line 2 are connected only by the liquid inlet 6. The gas that is displaced as the collection container 3 is filled with liquid can escape from the collection container 3 through a gas-permeable liquid barrier 5. The liquid barrier 5 is a fine-pored gas-permeable membrane that closes the collection container 3 and is impermeable for the liquid to be collected even at a relatively high pressure difference. When a collection container 3 is filled, the backup of the liquid at the gas-permeable liquid barriers 4 and 5 leads to an increase of the pressure in the supply line 2 until the weaker barrier 4 collapses. This initiates the filling of the next collection container 3 or continues the flow through the supply line 2. In a series of collection containers 3, the arrangement of the gas-permeable liquid barriers 4, 5 in accordance with the invention effects that the collection containers 3 are filled consecutively at a continuous flow of the liquid in the supply line 2.

All components of the sample collector 1 in accordance with the invention can be comprised of one or a plurality of substances such as glass, polypropylene and/or Teflon, which can be autoclaved and are chemically resistant. The sample collector 1 in accordance with the invention is suitable for production and for use as a disposable product. In a sample collector 1 in accordance with the invention, all hollow spaces and channels, including the collection containers 3, can be worked into a solid matter, for example pressed in or etched in. The sample collector 1 in accordance with the invention can be comprised of a single solid matter body or of a supply line 2 with integrated wetting barriers and collection containers that can be removed from said sample collector.

If the liquid barrier 5 is a fine-pored bacteria-proof membrane of polypropylene or Teflon, the samples can be removed with a cannula. The collection containers 3 can be connected to the supply line 2 with a slip joint so that the samples can be removed by detaching the slip joint. The method in accordance with the invention for the removal of a sample from a liquid flow consists of guiding the liquid from which the sample is to be removed into a supply line 2 with a collection container 3, a liquid barrier 4, and at least one liquid inlet 6.

In doing so, the fact that the liquid barrier 4 is impermeable for the sample liquid causes the collection container 3 arranged upstream of said barrier to fill up. After it is filled, the flow of liquid is stopped by the liquid inlet 6. This automatically causes the pressure difference between the part of the supply line 2 that is filled with liquid and the remaining part of the supply line 2 to rise, which causes the liquid barrier 4 to collapse and the flow of liquid through the supply line 2 to resume. If several collection containers 3 are connected to the supply line 2, they are filled consecutively in that one gas-permeable liquid barrier 4 after the other collapses when its critical pressure difference is exceeded. The interruption of the flow in the liquid inlet 6 may be effected by the backup at a more pressure-resistant gas-permeable liquid barrier 5 or in another way. One possible method for interrupting the flow in the liquid inlet 6 is icing the liquid inlet 6 after a specific filling level has been reached. For example, if the collection container 3 is connected to the supply line 2 by a liquid inlet 6 and the collection container 3 is cooled below the freezing point, the sample liquid that is dropped or flows into the collection container 3 will freeze. The gas discharge channel or the liquid inlet 6 will be closed by the formation of ice at a specific filling level, and the flow through the liquid inlet 6 is interrupted. A cooling of the sample liquid or the freezing of said sample liquid may also be advantageous for other reasons.

The movement and/or guiding of the liquid into the collection containers 3 can be performed at a constant flow rate, but also at a timely changeable flow rate. If the collection containers 3 have a defined volume, each collection container 3 can be assigned a specific volume, regardless of the flow rate. If the flow rate and the volume of the collection containers 3 are known, a specific filling time is obtained automatically for each deposited sample.

The type of the drive that moves and/or guides the liquid into the sample collector 1 in accordance with the invention is not significant for the method in accordance with the invention. All technical solutions that generate a pressure difference between the part of the supply line 2 that is filled with liquid and the remaining part of said supply line can be used for the method in accordance with the invention.

The method in accordance with the invention can be performed such that the collection containers 3 are filled with liquid consecutively at continuous flow. On the other hand, the flow also can be interrupted after each filling process or after a series of filling processes to perform the collection of the samples discontinuously according to the specific time schedule. To ensure that an interruption always occurs precisely after the filling of a collection container 3, advantage can be taken of the change of pressure in the supply line 2, which occurs inadvertently after the filling of the collection container 3. The pressure in the supply line 2 rises after the filling of a collection container 3 and drops again at the breakthrough through the gas-permeable liquid barrier 4. The aforementioned pressure can be measured with the pressure sensor 10 and used as a signal to interrupt the flow into the sample collector 1 by controlling an inlet valve 9 or the delivery pump 8 after one or a plurality of collection containers 3 have been filled. A time switch or an electronically memorized program can be used to end said interruption after a set timeline. In this way, the collection containers 3 can be filled in a preset longer time span or according to a preset longer timeline regardless of the pump rate. This is advantageous in particular if the collected samples of liquid are supposed to represent brief time segments over the course of an overall longer collection time period.

The applications of the automatic sample collector in accordance with the invention result from various advantageous properties. It can be produced and used advantageously as a disposable item to collect volume fractions from the sequence of a chromatography column, a reaction container, a fermenter, a dialysis- or ultra-filtration probe, a blood catheter and the like. To fix the components of the sample and/or to stop the growth of microbes, the collection containers 3 can comprise a protective gas or substances suitable for fixation, or they can be stored in a cooling apparatus. Due to the miniaturization of the sample collector 1 and its compact structure, it can be attached to animals or humans, and it can be provided with a Peltier-cooling arrangement to selectively cool the collection containers 3. Advantageous applications of the automatic sample collector in accordance with the invention are described in the following examples.

EXAMPLE 1

The sample collector 1 in accordance with the invention is used in an HPCL arrangement to collect fractions of oxygen-sensitive substances. Before the sample is applied and the sample collector 1 is attached, the column and the detector are rinsed with a buffer that is saturated with pure nitrogen. The applied sample collector 1 in accordance with the invention is closed on both ends and filled with pure nitrogen prior to application. The supply line 2, which serves as the gas discharge in accordance with FIG. 1a, ends in a cylinder with tight and slightly sliding piston. Because the HPLC-arrangement is operated at constant flow rate, the consecutively filled collection containers 3 can be attributed to the peaks recorded at the detector.

EXAMPLE 2

The sample collector 1, which is shown schematically in FIG. 1a, is used under water, for example to rake samples with a defined volume from the interstitial water of the root space of reed plants in the water, and to deposit them consecutively over the course of a longer analysis at randomly selectable times or according to a firmly established schedule. For this purpose, for example, a micro-filtration probe is inserted into the root area and connected to the sample collector 1 in accordance with the invention through a polypropylene hose. In the supply line 2 of the sample collector 1, the valve 9, a flow-limiting resistor in form of a capillary and the pressure sensor 10 are arranged successively upstream to the first collection container 3. Downstream from the last collection container 3, the supply line is connected to a larger negative pressure container, where the pressure is lowered by approximately 20 kPa relative to the atmospheric pressure. All components of the sample collector 1 are located under water. The flow-limiting resistor effects that the pressure difference relative to the atmospheric pressure applied in the negative pressure container is applied nearly unreduced at the pressure sensor 10 until the collection container 3 is filled with liquid. As soon as the gas-permeable liquid barrier 5 interrupts the flow, the pressure in the part of the supply line 2 that is filled with liquid increases until the gas-permeable liquid barrier 4 collapses and effects the flow-through. This causes the pressure at the pressure sensor 10 to drop again. The valve 9 is connected to a control arrangement that is set up such that it is closed if the pressure at the pressure sensor drops twice in succession. During each selected measuring period, two collection containers 3 are therefore filled, and the taking of samples is then temporarily interrupted. The second of the collection containers 3 used in the taking of samples is used for the analysis. This prevents a mixing of the samples to be analyzed and the small volume of liquid in the supply line 2. The valve 9 is opened at the desired time either manually or by means of an automatic control with a preset timer to fill the next two collection containers 3.

EXAMPLE 3

The sample collector 1 is used to remove bacteria-free samples from a fermenter in regular time intervals and deposit them consecutively for the purpose of analysis. For example, before the fermenter is autoclaved, the sample collector 1 in accordance with the invention is connected to a port integrated in the fermenter having a micro filter of autoclavable polypropylene or Teflon. The sample collector 1 is comprised of autoclavable polypropylene. After the last collection container 3, the gas-filled supply line 2 leads into a water-filled container with a water-filled discharge hose that is provided to connect a peristaltic pump. The fermenter and the attached sample collector 1 are autoclaved together. During the operation of the fermenter, samples are collected with the help of the peristaltic pump in accordance to a set time schedule.

EXAMPLE 4

The sample collector 1 is connected to the discharge of a dialysis device to remove underwater dialysis samples from the ground of a body of water according to a time schedule. The sample collector 1 used for this purpose has a gas discharge over a gas-permeable liquid barrier 5, which is independent of the supply line 2, as shown schematically in FIG. 1b. The gas-permeable liquid barrier 5 is adjacent to a gas discharge channel that is integrated in the sample collector 1 and connected to a gas discharge hose that projects from the water. A piston pump operated by battery or spring force is located in the inlet to the dialysis device. Pure water flows from a storage container into the dialysis device at a constant flow rate. The flow rate through the dialysis device is constant and below the critical flow for the adjustment of the diffusion balance for the analytes. It is chosen such that the collection containers 3 of the fraction collector are filled during the selected analysis period. In this way, a specific time period can be attributed to the filling of each collection container 3 with the dialysate.

EXAMPLE 5

The sample collector 1 is used to collect the samples separated by a capillary electrophoresis apparatus by electro-osmosis.

The sample collector 1 is comprised of a solid matter body of silicon, polypropylene or the like with integrated channels, filters and spaces that represent the supply line 2, the liquid inlet 6, the liquid barriers 4 and 5 as well as the collection containers 3 in accordance with FIG. 1b. The volume of the collection containers 3 is several µl, the volume of the remaining channels, i.e., the supply line 2, the liquid inlet 6 and the gas discharge 7, is fractions of one µl. The sample collector 1 is prepared by a tight connection between a base plate into which the supply line 2 and the connected collection containers 3 as well as the liquid barrier 4 were integrated, and a complementary cover plate, for example by bonding or pressing. The sample collector 1 comprises a gas discharge channel that is adjacent to a liquid barrier 5 and is delimited toward the outside by a silicon rubber diaphragm. To remove the sample, the diaphragm and the liquid barrier 5 are pierced with a capillary or a cannula.

EXAMPLE 6

The sample collector 1 is used to collect samples from a reactor container or living cell suspensions from a bio reactor and freeze them immediately after they are dropped into the collection containers 3. It has a Peltier cooling apparatus that allows for the collection containers 3 to be kept at a temperature below the freezing point of the water. The cooling is adjusted so that the temperature of the supply line 2 is above the freezing point of the water. The collection containers 3 are positioned vertically in the gravitational field and the supply line 2 is located above the collection containers 3, which are connected to it by a liquid inlet 6 and a gas discharge 7 (compare FIG. 1a). A liquid barrier 5 in the gas discharge is not required. As soon as the formed ice clogs up the gas discharge 7 of the collection container 3, the pressure of the liquid in the supply line 2 increases, the liquid barrier 4 collapses and the filling of the next connection container 3 begins.

EXAMPLE 7

The sample collector 1 is attached to the human or animal body and used for the analysis of the dynamics of a pharmaceutical drug. The collector containers 3 are, as shown in FIG. 1b, developed as blind ending channels with an approximately iso-diametric 4-mm cross-section and a length of 2 cm. The liquid inlet 6 is a channel of 1-mm width. At the end of the collection container 3 relative to the supply line 2 is a gas-permeable liquid barrier 5 in the form of a fine-pored polypropylene membrane with 200-nm pore width, as shown schematically in FIG. 1b. After each branch-off of an inlet 6 to a collection container 3, the supply line 2 has a polypropylene capillary with a diameter of 200 µm as gs-permeable liquid barrier 4. The supply line 2 ends after the last collection container 3 with a fine-pored polypropylene membrane. All flown-through parts are autoclaved. The sample collector 1 is attached to a blood withdrawal catheter and connected to a battery-operated micro-hose pump as delivery apparatus 8 which, as shown in FIG. 1a, is located on the supply line 2 upstream to a pressure sensor 10. The change in pressure which occurs after the filling of a collection container 3 is used as signal for the temporary interruption of the pumping process. The pump is connected to a programmable control apparatus and switched on after each interruption according to a programmed time schedule and then off again when the next collection container 3 has been filled. When all collection containers 3 have been filled and the liquid backs up at the fine-pored polypropylene membrane at the end of the supply line 2, a higher backup pressure level is reached. This is used as a signal to end the pump program.

The invention is not limited to the embodiments described herein. Rather, it is possible to realize additional development variants through the combination and modification of the aforementioned means and characteristics without leaving the scope of the invention.

LIST OF REFERENCE SYMBOLS

1 Automatic sample collector
2 Supply line
3 Collection container
4 Gas-permeable liquid barrier that collapses at a limited pressure difference
5 Pressure-resistant gas-permeable liquid barrier
6 Liquid inlet
7 Gas discharge
8 Delivery apparatus
9 Valve
10 Pressure sensor

The invention claimed is:

1. Automatic sample collector for chronological deposition of liquids having
   a plurality of collection containers arranged in series, each connected to a supply line through a liquid inlet,
   a supply liquid barrier located in the supply line after each liquid inlet that is gas-permeable in dry condition and becomes permeable to liquids after contact with the liquid and after a defined pressure difference thereover is exceeded and on the basis of wetting resistances, and
   a second gas-permeable liquid barrier on the basis of wetting resistances being integrated into the collection container for preventing the inflow to the collection container through the liquid inlet after the collection container has been filled, wherein the collapse of said second gas-permeable liquid barrier requires a greater pressure difference thereover than the collapse of the supply liquid barrier.

2. Automatic sample collector in accordance with claim 1, wherein
   the gas-permeable liquid barrier is connected directly to the atmosphere or is integrated into a gas discharge.

3. Automatic sample collector in accordance with claim 1, wherein
   each gas discharge is connected to the supply line and the supply liquid barrier is arranged between the liquid inlet and the gas discharge of the collection container.

4. Automatic sample collector in accordance with claim 1, wherein the collection container is connected to a gas discharge that is not connected to the supply line but rather in another way to the atmosphere or another larger closed space.

5. Automatic sample collector according to claim 1, wherein the collection containers can be detached from the supply line.

6. Automatic sample collector in accordance with claim 1, wherein
   a delivery apparatus in form of a pump, suction apparatus or a valve is integrated in the supply line, and
   wherein the supply line comprises a pressure sensor, and
   a controller is configured to control the delivery apparatus or the valve in order to interrupt the liquid flow by switching off the pump or the valve as a result of the change in pressure on the collapse of the gas-permeable liquid barrier, and in order to resume the flow.

7. Automatic sample collector in accordance with claim 1, characterized in that the collection containers can be detached from the supply line.

8. Automatic sample collector in accordance with claim 1, characterized in that a delivery apparatus in form of a pump or suction apparatus is integrated in the supply line.

9. Automatic sample collector in accordance with claim 1, characterized in that a valve is integrated in the supply line.

10. Automatic sample collector in accordance with claim 1, characterized in that the supply line comprises a pressure sensor.

11. Automatic sample collector in accordance with claim 8, characterized in that a control is arranged for the delivery apparatus or the valve.

12. Automatic sample collector in accordance with claim 1, wherein gas-filled cavities of the sample collector contain a protective gas.

13. Automatic sample collector in accordance with claim 1, characterized in that a cooling apparatus, for the collection containers is integrated in the sample collector.

14. Automatic sample collector in accordance with claim 1, characterized in that an apparatus that prevents the flow in the liquid inlet after the filling the collection container is developed as cryostat which maintains the temperature of the liquid in the supply line above the freezing point and the temperature in the collection containers below the freezing point of the liquid to be collected.

15. Method extracting a sample from a flow of liquid, comprising
- guiding the liquid in a supply line of a sample collector to a gas-permeable liquid barrier on the basis of wetting resistances and which becomes permeable to liquids after contact with the liquid and after a defined pressure difference thereover is exceeded and guiding the liquid via a liquid inlet that branches off from the supply line upstream of the gas-permeable liquid barrier and runs into a collection container,
- then filling said liquid into the collection container through the liquid inlet,
- then interrupting the feed-in of the liquid through the liquid inlet by a second gas permeable liquid barrier on the basis of wetting resistances, wherein collapsing the second gas-permeable liquid barrier requires a greater pressure difference thereover than collapsing the supply liquid barrier,
- the second gas-permeable liquid barrier being integrated into the collection container, whereupon
- a pressure in the collection container increases,
- the liquid barrier is permeated after a defined pressure difference thereupon is exceeded and
- the liquid continues to flow through the supply line.

16. Method in accordance with claim 15, comprising measuring the pressure difference between the liquid in the supply line and a reference pressure using
- the increase of pressure in the supply line after filling a sample container, or
- the decrease of said pressure after collapse of the liquid barrier as a signal to interrupt the feed-in of the liquid in the supply line with the help of a valve or a controllable pump.

17. Method in accordance with claim 16, further comprising after interruption, automatically or manually resuming the feed-in of liquid at a defined time by the controlling a valve or a delivery apparatus.

18. Method in accordance with claim 15 wherein removal of a plurality of samples is a chronological deposit of liquid samples from a flow of liquid without using movable parts and without an external energy source.

19. Method in accordance with claim 15 wherein removal of a plurality of samples is a chronological deposit of liquid fractions under water or in a protective gas atmosphere.

20. Method in accordance with claim 15 further comprising chronologically freezing liquid samples.

21. Method in accordance with claim 15 wherein removal of a sample is from a chromatography column, an electrophoresis apparatus, a reaction container, a culture container, a fermenter, a body of water, the ground of a body of water, the ground, a vegetable, or animal or human tissue or organ.

* * * * *